United States Patent
Mackay et al.

(10) Patent No.: US 8,420,875 B1
(45) Date of Patent: Apr. 16, 2013

(54) CONVERSION OF WASTE PLASTICS TO LIQUID HYDROCARBON PRODUCTS

(75) Inventors: Ian Mackay, Eden Prairie, MN (US); Karl Greden, Hinckley, MN (US)

(73) Assignee: Rational Energies, LLC, Eden Praire, MN (US)

( * ) Notice: Subject to any disclaimer, the term of this patent is extended or adjusted under 35 U.S.C. 154(b) by 0 days.

(21) Appl. No.: 13/427,892

(22) Filed: Mar. 23, 2012

Related U.S. Application Data

(60) Provisional application No. 61/583,443, filed on Jan. 5, 2012.

(51) Int. Cl.
*C07C 4/04* (2006.01)

(52) U.S. Cl.
USPC ............ 585/241; 241/23; 241/24.18; 241/29; 208/131; 208/132

(58) Field of Classification Search ........................ None
See application file for complete search history.

(56) References Cited

U.S. PATENT DOCUMENTS

| | | | | |
|---|---|---|---|---|
| 369,882 | A | * | 9/1887 | Sass et al. ........................ 24/622 |
| 5,904,879 | A | * | 5/1999 | Winter et al. .................. 252/373 |
| 5,908,165 | A | * | 6/1999 | Guschall et al. ................. 241/23 |
| 5,917,102 | A | * | 6/1999 | Holighaus et al. ............. 585/241 |
| 7,757,974 | B2 | * | 7/2010 | Hofmann et al. .................. 241/3 |
| 7,897,436 | B2 | * | 3/2011 | Bouche et al. ................. 438/118 |
| 2010/0043988 | A1 | * | 2/2010 | Hofmann et al. ............... 162/28 |
| 2010/0155979 | A1 | * | 6/2010 | Hofmann et al. .......... 264/37.26 |
| 2012/0304536 | A1 | * | 12/2012 | Bai ................................ 44/589 |

* cited by examiner

*Primary Examiner* — Tam M Nguyen

(74) *Attorney, Agent, or Firm* — Henry E. Naylor

(57) ABSTRACT

The conversion of waste plastics material to hydrocarbon fuel products, particularly transportation fuels. The waste plastics material can be obtained from any suitable source, such as a municipal solid waste facility and from agricultural and horticultural activity. The plastics material feed, which can contain from about 10 to about 50 wt. % dirt, is reduced to an effective size, then dried, if needed, to a moisture level of 2 wt. % and less, then screened to removed dirt, then densified into nuggets of at least about 10 lb/ft$^3$, then pyrolyzed.

16 Claims, No Drawings

CONVERSION OF WASTE PLASTICS TO LIQUID HYDROCARBON PRODUCTS

CROSS-REFERENCE TO RELATED APPLICATIONS

This application is based on Provisional Application 61/583,443 filed Jan. 5, 2012.

FIELD OF THE INVENTION

This invention relates to the conversion of waste plastics material to hydrocarbon fuel products, particularly transportation fuels. The waste plastics material can be obtained from any suitable source, such as a municipal solid waste facility and from agricultural and horticultural activity. The plastics material feed, which can contain from about 10 to about 50 wt. % dirt, is reduced to an effective size, then dried, if needed, to a moisture level of 2 wt. % and less, then screened to removed dirt, then densified into nuggets of at least about 10 lb/ft$^3$, then pyrolyzed.

BACKGROUND OF THE INVENTION

There is a steadily increasing demand for technology capable of converting discarded and waste plastic materials into higher value products. This is due in large measure to public concern over potential environmental damage caused by the presence of such waste materials. Plastics waste is the fastest growing waste product, with about 30 million tons in 2009, compared to 18 million tons in 1995 and only 4 million tons in 1970. This amount is growing at more than 10% per year. In 2009 the 30 million tons of plastic waste represented about 12 wt. % of total municipal solid waste (MSW). Transforming plastic waste material into useful products presents a unique opportunity to address the growing environmental concerns Of the 30 million tons of waste plastics in 2009, about 13 million tons was in the form of containers and packaging, about 11 million tons was in the form of durable goods, such as appliances, and about 7 million tons was in the form of non-durable goods, such as plates, cups, etc. While great effort is being made to recover and recycle as much waste plastics as possible, there are various challenges that must be met for cost effective recycling. For example, waste plastics are typically composed of a variety of different plastic types, some of which are not compatible with one or more other types depending on the desired end products. For example, when different types of plastics are melted together they tend to phase-separate and set into layers. The phase boundaries between layers lead to structural weakness in the resulting blend of material, thus, such reconstituted polymer blends are only useful in limited applications. Another barrier to recycling of plastics is the widespread use of dyes, fillers and other additives used in the manufacture of the original plastic products. A melt of plastics waste is generally too viscous to economically remove fillers, and would be damaged by many of the processes that could potentially remove the added dyes.

One use for waste plastics that can add to the alternative energy pool is to convert at least a fraction of the waste plastics to a hydrocarbon transportation fuel, such as a gasoline, diesel fuel, etc. There is an increasing demand for alternative energy sources and transportation fuels. While a mixture of waste plastic types can, in general, be used as a feedstock for its conversion to transportation fuels, any polyvinyl chloride (PVC) or polyethylene terephthalate (PET) plastics material component of the plastics feedstock will have to be kept to a minimum. When PET and/or PVC is included in the feedstock acids are formed that can result in corrosion of metal parts of processing equipment and to an acidized oil product.

Although there are myriad processing schemes for producing transportation fuels from non-petroleum sources, as well as myriad processing schemes for recycling waste plastics, there is still a need in the art for processes that are capable of converting waste plastics to higher value products in a cost effective manner.

SUMMARY OF THE INVENTION

In accordance with the present invention there is provided a process for converting waste plastics material to liquid hydrocarbon products, which process is comprised of:

a) receiving a feedstream comprised of from about 10 to about 50 wt % dirt and at least one type of plastic having a bulk density less than about 10 lb/ft$^3$, wherein if only one type of plastic is received it will be of a type other than a polyethylene terephthalate or a polyvinyl chloride;

b) comminuting the plastics of said feedstream to an effective size;

c) drying said comminuted waste plastics material to less than 2 wt. % water content in the event that the waste plastics material has in excess of 2 wt. % water content;

d) removing substantially all dirt from said plastics material;

e) densifying said comminuted plastics in an agglomeration zone wherein its' bulk density in increased to a value of at least about 10 lb/ft$^3$;

f) conducting said densified plastics material of step e) above to a pyrolysis zone where it is heated, in the substantial absence of oxygen, to a temperature from about 150° C. to 600° C. thereby converting a least a fraction of the densified plastic material to a gaseous hydrocarbon phase;

g) conducting said gaseous hydrocarbon phase to a condensing zone wherein at least one liquid hydrocarbon product is condensed from said gaseous hydrocarbon phase; and h) recovering the one or more condensed liquid hydrocarbon product.

In one preferred embodiment, the plastics waste material is co-processed with up to about 50 wt. % of a petroleum-based waste hydrocarbon material.

In another embodiment, the transportation fuel products from practice of the present invention are selected from a gasoline boiling range hydrocarbon stream to a #5 fuel oil product stream.

DETAILED DESCRIPTION OF THE INVENTION

The present invention is directed to a process for converting plastic materials, preferably waste plastics material, to liquid hydrocarbon products. Preferred liquid hydrocarbon products include transportation fuels, preferably gasoline and fuel oil boiling range fuels including diesel and jet fuels. That is, hydrocarbon fuels boiling in the range from about 70° C. to about 500° C. and which are comprised predominantly of a mixture of aromatics and saturated and unsaturated non-aromatic hydrocarbons having carbon numbers from about 5 to about 35.

Any plastic material can be used in the practice of the present invention, but for economic reasons waste plastics material are preferred that are substantially free of PET and PVC. The waste plastics material used in the present invention can be obtained from any suitable source, such as from municipal solid waste, from agricultural and horticultural activities, as well as waste plastic generated at manufacturing facilities. The plastics material used in the practice of the present invention will often come from specialized MSW processing facilities designated Plastics Material Recovery Facilities (PMRF). In these facilities, raw MSW is fed to a processing line that can be part of and overall plastics conversion plant or it can be a separate facility. The MSW is typically subjected to a series of sorting mechanisms at the PMRF to separate the waste plastics from other recyclable materials, principally ferrous and non-ferrous metals, with the residue being sent to disposal. Steps are also typically taken at the PMRF to remove PET plastic for technical and economic reasons. First, waste PET (usually from used water bottles, etc.) is a well-established commodity having a profitable resale value. In addition, pyrolysis of PET, as well as PVC, has relatively poor conversion efficiency and leads to the formation of terephthalic acid and hydrochloric acid, respectively, which if not separated from the plastics feed will result in an undesirable acidized oil product. Thus, it is preferred that the plastics material feed contain less than about 10 wt. %, preferably less than about 5 wt. %, more preferably less than about 3 wt. %, and most preferably substantially no PET or PVC.

In a typical PMRF design, the raw MSW is usually tipped onto a tipping floor and after removal of oversized bulky waste is moved via a front-end loader onto a metering conveyor, then onto a picking belt where easily recognizable items, such as large plastic items, ferrous metals, film plastics, and non-ferrous metals are removed and manually sorted by pickers. Following this manual sort, incoming garbage bags are opened in a bag breaker to release their contents, which is then typically screened to about 2 inches to remove undersized material such as broken glass, grass, small organics, small stones, and dirt. About half of the incoming MSW is removed at this point. The larger material (>2 inches) is typically fed to an air classifier that applies a stream of air to the passing material to separate the lighter materials such as plastic, paper, and aluminum from heavier metal and non-plastic items. The heavier items, that usually constitute about 8 percent of the material flow, are removed from the stream as so-called "heavies". A second air classifier is normally used which acts on the light material to remove film plastics that are sent to a plastics baler. A magnet is usually used to separate the ferrous metal items form the stream containing heavier materials. The remaining items are subjected to a manual check to recover any plastics before being disposed of as residue.

The light items, minus the film plastics, are sent to a second screen that acts as a polishing step to remove any remaining small-scale items of less than about 2 inches. Undersized material is disposed of as residue and the stream of larger material is subjected to a magnetic field to remove residual ferrous metal. Material that passes through the magnetic field is sorted using a suitable first separator that conventionally uses infrared sensors to identify PET items and is followed by blasts of compressed air to separate the PET from the material stream. This results in a PET stream suitable for recycling and a reject stream that contains mixed waste plastics. This second stream is usually sent to an eddy current separator that generates a strong magnetic field that repels aluminum items and other non-ferrous items from the material stream. The aluminum items and other non-ferrous items can be collected for recycling. The remaining material after the eddy current separator is sent to a second separator zone to specifically remove the desired mixed waste plastics from the stream using infrared sensors. The resulting plastics stream is sent to a plastics baler. The reject stream from the second separator can be disposed of as residue. One or more recycled plastics streams are produced and are typically baled and sold to customers who convert the recycled baled plastics material to useful products. While the above represents a typical conventional method for separating various components of MSW, the practice of the present invention does not limit itself to receiving plastic materials substantially free of debris, such as dirt, or for plastic streams comprised of principally one type of plastic material, although it is preferred that little, or substantially no, PVC be present in the plastic feedstock.

Non-limiting examples of waste plastic materials suitable for use herein, especially those obtained from MSW, will generally include one or more plastics selected from the group consisting of: high-density polyethylene (HDPE) which is generally used for milk bottles; low density polyethylene (LDPE) which is used for carrier bags and bin liners; polypropylene (PP), which is used for such things as margarine tubes and microwaveable meal trays; polystyrene (PS) which is used for yoghurt pots, foam meat or fish trays, egg cartons, vending cups and plastic cutlery, as well as myriad other plastics in smaller quantities. Unlike conventional plastic-to-oil conversion processes, practice of the present invention is considerably more tolerant of contaminants, such as dirt and other debris.

The plastics material that is used as feedstock for the practice of the present invention can be received for use in either baled or non-baled form from a PMRF or directly from another source such as an agricultural or industrial supplier. If baled, the bales are broken open and the plastic material is fed to a shredder and shredded to an effective size that will typically be from about 4 inches or less, preferably from about 2 to 4 inches. If the plastic material is received in a size already 4 inches or less, then it is preferred that no additional shredding be done. It will be noted that some waste plastic, especially those received from agricultural uses can contain up to about 50% by weight, or more, of dirt, moisture and other contaminants.

Following the shredding, the remaining plastics material feedstock is further cleaned to remove dirt and moisture adhering to the material in order to allow for proper densification and to maximize pyrolysis product yield. Conventional plastics to liquid hydrocarbon technology teaches that waste plastics contaminated with fines should be washed prior to densification. However, washing and subsequent water treatment operations are expensive and limit the economics of the overall process. The inventors hereof have discovered however that drying the waste plastics to a level of approximately 2% moisture, or less, reduces the fines adherence such that a vibratory screen can be employed to sufficiently clean the material for further processing. In a preferred embodiment of this invention the plastic is dried using a fluidized bed dryer operating at about 90° C. to about 110° C., preferably from about 90° C. to about 100° C. and the vibratory screen utilizes an 8 mesh screen. This method is particularly effective when preferably used in combination with the agglomeration, or densification method of the present invention. The density of a typical waste plastics feed will be substantially less than the desired 10+ lb/ft$^3$. Most plastic agglomeration methods today utilize heat to partially or completely melt the plastic, then fed through augers to force the molten material through a die and cutter. Such a method is typically energy intensive and sensitive to contamination because tramp material can plug the die or damage the cutter. It is preferred that agglomeration be performed by a system comprising a cylindrical vessel containing one or more blades that densify the plastics material through a mixing action and frictional heating caused by the spinning blades. In this case, the waste plastic is conducted to an agglomeration zone wherein the plastic material is densified to a density greater than 10 lb/ft$^3$, preferably between about 10 and 25 lbs/ft$^3$, more preferably from about 12 to 22 lbs/ft$^3$, and most preferably from about 18 to 22 lbs/ft$^3$. As previously mentioned, this practice of the present invention can tolerate substantially more contamination than conventional plastics cleaning and densification processes. In fact, the plastics feedstock for the present invention will contain from about 10 to about 50 wt/% dirt, preferably from 15 to 40 wt. % dirt, more preferably from about 15 to 30 wt. % dirt, wherein all weight percents are based on the total weight of plastics plus and dirt. It is preferred that any dirt present be at an average particle size of less than about 0.5 inches, more preferably less than about 0.25 inches, even more preferably less than about ⅛ of an inch, and most preferably less than about 1/32 inch. The term "dirt" as used herein means non-metallic inorganic materials non-limiting examples which include dirt, soil, sand, dust, earth, mud, and grime. The dirt that will be most likely be included with the plastics material for purposes of the present invention is dirt, or earth, from agricultural fields wherein plastic sheeting is extensively used. In addition, as noted, conventional techniques for preparing plastics material for pyrolysis typically requires the use of considerably more energy and water because of more elaborate washing, melting, and extrusion steps.

The densified plastics material feedstock of the present invention is conducted to a thermal conversion zone where it is heated to a temperature where it is melted and converted to hydrocarbon products, preferably gaseous hydrocarbon products. The preferred thermal process is pyrolysis that can be either catalytic or non-catalytic. It is preferred to use non-catalytic pyrolysis. Pyrolysis is a thermochemical process for the decomposition of organics conducted at elevated temperatures in the substantial absence of oxygen. Pyrolysis typically occurs under pressure and at operating temperatures of about 150° C. to about 600° C., preferably from about 300° C. to about 600° C., and more preferably from about 420° C. to about 550° C. The pyrolysis step can be vacuum pyrolysis wherein the waste plastics material is heated in a vacuum in order to decrease boiling point and to avoid adverse chemical reactions. Since pyrolysis is endothermic, heat must be provided for the pyrolysis reaction to occur. Non-limiting examples of ways heat can be provided include partial combustion of a fraction of the pyrolysis products, direct heat transfer with a hot gas, indirect heat transfer with exchange surfaces, and direct heat transfer with circulating solids.

The waste plastics material is converted by thermal degradation (cracking) in the substantial absence of oxygen. The plastics are typically first made molten within a steel reaction chamber under vacuum; or with use of an inert purging gas, such as nitrogen. The chamber continues to be heated to transform the molten material to a gaseous state. Hot pyrolytic gases comprised of hydrocarbons of the desired carbon length range are then condensed in one or more condensing zones to yield one or more hydrocarbon distillate end products comprising straight and branched chain aliphatics, cyclic aliphatics and aromatic hydrocarbons.

The pyrolysis step of the present invention is not limited to the above process scenario. Any suitable pyrolysis process scheme can be used in the present invention as long as it can handle plastic material having a density of greater than 10 lbs/ft$^3$ and contain from about 10 to about 50 wt. % dirt as previously mentioned. In a preferred embodiment the pyrolysis step of the present invention is practiced in the manner disclosed by Agilyx Corporation that starts with a plastic feed material having the size range of ½ inch minus. This plastics material is loaded into cartridges, which are sometimes referred to as direct contact cartridges. Once filled, a lid is put in place and the closed cartridge is moved to a pyrolysis zone wherein the cartridges are heated using combustion gases from a burner system to depolymerize the plastics. The filled cartridges are subjected to temperatures up to about 600° C. with the temperature inside of the cartridges reaching about 425° C. At this temperature, the plastics melt and break down to petroleum gases, which are drawn off using a slight vacuum of about 10 negative inches of water column, then sent to a series of condensers where the gases are condensed to products. The product yield is dependent on the plastic feedstock such that plastics with low oxygen content, such as HDPE, LDPE provide the highest oil yield, and plastics with a relatively high oxygen or chlorine content, such as PET or PVC, result in dramatically reduced yields. It is for this reason that PET and PVC quantities are limited, and preferably eliminated from the plastic feedstream.

The preferred pyrolysis process noted above can be improved by managing the temperature ramp rate, peak temperature and soak times of the densified plastics material to increase the production and yield of the preferred hydrocarbon liquids. By increasing the temperature ramp rate and the maximum temperature, the yield of hydrocarbon liquids will be increased by reducing char production and will decrease the average hydrocarbon chain length to the preferred range. Decreasing the time at the maximum temperature will increase the production of the preferred hydrocarbon liquid by decreasing the average carbon chain length in the product by leaving behind longer chain molecules. In a preferred embodiment of the present invention a heavy liquid fraction that is a compatible blend stock for a #5 fuel oil (ASTM D396) is produced. Lighter liquid fractions can be separately condensed and further refined in a preferred embodiment utilizing a reformer column operating at about 75° C. to produce a stabilized gasoline or jet fuel blend stock. Reforming is a well-known refinery process and no further discussion is needed for purposes of this invention.

It is within the scope of this invention that the waste plastics material be co-processed with up to about 50 wt. % (based on the total weight of feedstock including co-feed) of a waste petroleum-based hydrocarbon material. Non-limiting examples of waste petroleum-based hydrocarbon material that can be used in the practice of this invention includes used motor oil, machine oil, off-spec fuels, greases, waxes, and asphalt. Preferred is used motor oil.

It was further discovered that fuel gas produced during the preferred pyrolysis process which is preferably flared can be subjected to a heat recovery system to improve operating efficiency of the facility. The recovered heat is sufficient to significantly reduce utility requirements for both the drying operation and the reformer operation.

What is claimed is:

1. A process for converting waste plastics material to hydrocarbon products, which process is comprised of:
    a) receiving a feedstream comprised of from about 10 to about 50 wt. % dirt and at least one type of plastic having a bulk density less than about 10 lb/ft$^3$, wherein if only one type of plastic is received it will be of a type other than a polyethylene terephthalate or a polyvinyl chloride;
    b) comminuting the plastics of said feedstream to an effective size;
    c) drying said comminuted waste plastics material to less than 2 wt. % water content in the event that the waste plastics material has in excess of 2 wt. % water content;
    d) removing substantially all dirt from said plastics material;

e) densifying said comminuted plastics in an agglomeration zone wherein its' bulk density in increased to a value of at least about 10 lb/ft$^3$;

f) conducting said densified plastics material of step e) above to a pyrolysis zone where it is heated, in the substantial absence of oxygen, to a temperature from about 150° C. to 600° C. thereby converting a least a fraction of said densified plastics material to a gaseous hydrocarbon phase;

g) conducting said gaseous hydrocarbon phase to a condensing zone wherein at least one liquid hydrocarbon product is condensed from said gaseous hydrocarbon phase; and h) recovering the at least one condensed liquid hydrocarbon product.

2. The process of claim 1 wherein the feedstream contains from about 15 to about 40 wt. % dirt.

3. The process of claim 1 wherein at least one hydrocarbon product has an average boiling point ranging from 150° C. to 500° C.

4. The process of claim 1 wherein two or more hydrocarbon product streams are produced.

5. The process of claim 4 wherein at least one of said two or more hydrocarbon product streams is sent to downstream refining to result in a transportation fuel selected from the group consisting of gasoline, diesel, and jet fuel.

6. The process of claim 1 wherein a petroleum-based waste hydrocarbon material is co-processed with the plastics waste.

7. The process of claim 6 wherein the amount of petroleum-based waste hydrocarbon material, based on the total weight of plastics material and petroleum-based hydrocarbon material is up to about 50 wt. %.

8. The process of claim 7 wherein the petroleum-based waste hydrocarbon material is selected from the group consisting of motor oil, machine oil, off-spec fuels, greases, waxes, and asphalt.

9. The process of claim 1 wherein the at least one type of plastics feedstream is selected from the group consisting of high-density polyethylene, low density polyethylene, polypropylene, and polystyrene.

10. The process of claim 1 wherein a plurality of types of plastics comprise the feedstream, one of which is selected from polyvinyl chloride, and polyethylene terephthalate.

11. The process of claim 10 wherein the plastics feedstream is subjected to a screening stage wherein substantially all of any polyvinyl chloride, and polyethylene terephthalate are removed.

12. The process of claim 1 wherein the effective size of the plastics material, after comminuting, is from about 2 to 4 inches.

13. The process of claim 1 wherein pyrolysis is performed at a temperature in the range of about 300° C. to about 600° C.

14. The process of claim 13 wherein the pyrolysis is performed in the temperature range of about 420° C. to about 600° C.

15. The process of claim 1 wherein the density of the feedstream, after said densifying step, is from about 10 to 25 lbs/ft$^3$.

16. The process of claim 15 wherein the density is from about 12 to 22 lbs/ft$^3$.

* * * * *